United States Patent [19]

Persson et al.

[11] Patent Number: 5,221,390
[45] Date of Patent: Jun. 22, 1993

[54] METHOD AND APPARATUS FOR POSITIONING AT LEAST ONE THREAD, BAND OR THE LIKE IN A PRE-DETERMINED PATTERN ON A MATERIAL WEB

[75] Inventors: Lennart Persson, Göteborg; Dan Johansson, Västra Frölunda, both of Sweden; Leidulf Indrebo, Jersoy, Norway

[73] Assignee: Molnlyke AB, Gothenborg, Sweden

[21] Appl. No.: 634,881

[22] PCT Filed: Jul. 6, 1989

[86] PCT No.: PCT/SE89/00390
§ 371 Date: Feb. 28, 1991
§ 102(e) Date: Feb. 28, 1991

[87] PCT Pub. No.: WO90/00514
PCT Pub. Date: Jan. 25, 1990

[30] Foreign Application Priority Data

Jul. 12, 1988 [SE] Sweden .................. 8802607-5

[51] Int. Cl.⁵ .................................. B65H 57/28
[52] U.S. Cl. .................................. 156/164; 28/101; 156/177; 156/179; 156/439; 156/440
[58] Field of Search .............. 156/164, 177, 178, 179, 156/439, 440, 441, 181, 433, 436; 28/101, 102, 149, 150, 151, 152, 289; 66/84 A; 604/385.2

[56] References Cited

U.S. PATENT DOCUMENTS

| 1,804,916 | 5/1931 | Cotte ................ 156/440 |
| 2,548,568 | 4/1951 | Crise ................ 156/70 |
| 2,962,080 | 11/1960 | Hirsch ................ 28/102 |
| 3,321,348 | 5/1967 | Rupp ................ 156/177 |
| 3,340,584 | 9/1967 | Kalwaites ................ 28/101 |
| 3,594,256 | 7/1971 | Schuller et al. ................ 156/440 |
| 3,607,565 | 9/1971 | Eaton ................ 156/440 |
| 3,616,067 | 10/1971 | Treckmann ................ 156/441 |
| 3,828,367 | 8/1974 | Bourgeois ................ 156/164 |
| 3,829,339 | 8/1974 | Pinette ................ 156/179 |
| 3,902,644 | 9/1975 | Bous ................ 226/44 |
| 3,905,067 | 9/1975 | Keib et al. ................ 19/156 |
| 3,921,265 | 11/1975 | Eschenbach ................ 156/440 |
| 4,052,239 | 10/1977 | Chen ................ 156/177 |
| 4,064,916 | 12/1977 | Dagneb ................ 140/2 |
| 4,172,748 | 10/1979 | Petzetakis ................ 156/177 |
| 4,293,367 | 10/1981 | Klasek et al. ................ 156/164 |
| 4,578,141 | 3/1986 | Gidge et al. ................ 156/439 |
| 4,588,462 | 5/1986 | Horowitz et al. ................ 156/439 |
| 4,692,163 | 9/1987 | Widlund et al. ................ 604/385.2 |
| 4,715,924 | 12/1987 | McConnell ................ 156/181 |
| 4,726,873 | 2/1988 | Ales et al. ................ 156/495 |
| 4,735,672 | 4/1988 | Blad ................ 156/433 |
| 4,776,911 | 10/1988 | Uda et al. ................ 156/164 |
| 4,897,084 | 1/1990 | Ternstrom et al. ................ 604/385.2 |

FOREIGN PATENT DOCUMENTS

| 584551 | 10/1959 | Canada .................. 28/289 |
| 048010 | 3/1982 | European Pat. Off. .......... 156/164 |
| 251251 | 1/1988 | European Pat. Off. .......... 156/164 |
| 158240 | 4/1988 | Norway . |

Primary Examiner—Michael W. Ball
Assistant Examiner—Steven D. Maki
Attorney, Agent, or Firm—Burns, Doane, Swecker & Mathis

[57] ABSTRACT

The present invention relates to a method for positioning at least one thread, band or like element in a pre-determined pattern above a conveyor path with the aid of thread outfeed device having at least one thread outlet device. In accordance with the invention, the thread outlet, or each thread outlet, is moved in a simple or a composite rotational path in a plane parallel with the conveyor path, and the path is moved linearly in relation to the rotational axis of the thread outlet. This will cause the thread outlet to move in a spiral-like movement path relative to the conveyor path. The conveyor path has mounted thereon dogging elements which are located within the spiral-like movement path of the thread outlet, such as to enable the thread to be laid out in a pattern determined by the dogging elements. The invention also relates to apparatus for carrying out the method.

31 Claims, 8 Drawing Sheets

METHOD AND APPARATUS FOR POSITIONING AT LEAST ONE THREAD, BAND OR THE LIKE IN A PRE-DETERMINED PATTERN ON A MATERIAL WEB

The present invention relates to a method and apparatus for positioning at least one elastic thread, band or like element in a pre-determined pattern on a sheet material web for a disposable absorbent article with the aid of a thread outfeed means and a thread outlet. The method and apparatus are particularly intended for laying out elastic threads intended to form the leg and waist elastic of diapers.

It is known in the manufacture of so-called disposable diapers to provide the diapers with leg elastic, so that the diaper will fit snugly around the thighs of the wearer. For reasons of manufacture, the elastic threads used to this end in known diapers are placed in mutually parallel relationship. An example of such diapers is found described and illustrated in U.S. Pat. No. 3,860,003. These diapers comprise absorbent pads of hour-glass configuration, the narrow central part of which is located centrally between the wearer's legs in use. The use of elastic threads which extend in straight, mutually parallel lines in the longitudinal direction of the diaper, however, results in chafing against the wearer's skin, on the inward sides of the thighs.

It is also known to position the elastication in a V-shape pattern, in which the elastic intersects the absorbent pad in the vicinity of the crotch part of the diaper. Diapers which are provided with this type of elastication will better conform to the contours of the wearer's body than a diaper manufactured in accordance with the aforesaid U.S. patent specification, besides avoiding unpleasant chafing of the wearer's crotch.

It is also known to arrange elastic threads in a diamond or network configuration and to produce curved leg elastic similar to that used in tailored leg apparel. One method of producing such elastication is described and illustrated in our Swedish Patent Specification 8406071-4.

It is also conceivable to lay elastic threads in a curved path on a continuously advancing web of material, for instance by guiding the thread laying devices electrically, in a backward and forward motion across the web. Such a method of manufacture, incorporating rapid transfer movements, will be complicated, however, particularly in the case of high speed manufacturing lines.

Our Swedish Patent Application 8801324-8 teaches a method and apparatus for laying out elastic threads or filaments in a curved path, with the aid of one or more rotating rolls which have peripherally arranged thread-guiding grooves or slots.

The object of the present invention is to provide a method of the aforesaid kind which will ensure uniform tension in the laid threads; which will enable the threads to be laid with good precision; which can be effected with the aid of only a few moveable components; which will enable the threads to be laid out at high speeds; and which will enable the threads to be laid out in mutually different patterns.

This object is achieved in accordance with the invention by means of a method having the characteristic features set forth in claim 1. Because the thread outlet need only be given a rotational movement, the threads can be laid out at high speeds. This renders the inventive method highly suitable for laying out elastic threads in the manufacture of diapers. Furthermore, the threads can be laid out with great precision, since the precision concerned in the present respect is dependent solely on the accuracy at which the thread dogging elements, thread carriers or like devices are positioned.

The invention also relates to apparatus for carrying out the inventive method, the characteristic features of which apparatus are set forth in the following claim 8.

So that the invention will be more readily understood, a number of exemplifying embodiments of the invention will now be described in greater detail with reference to the accompanying drawings, in which.

Figure 1:
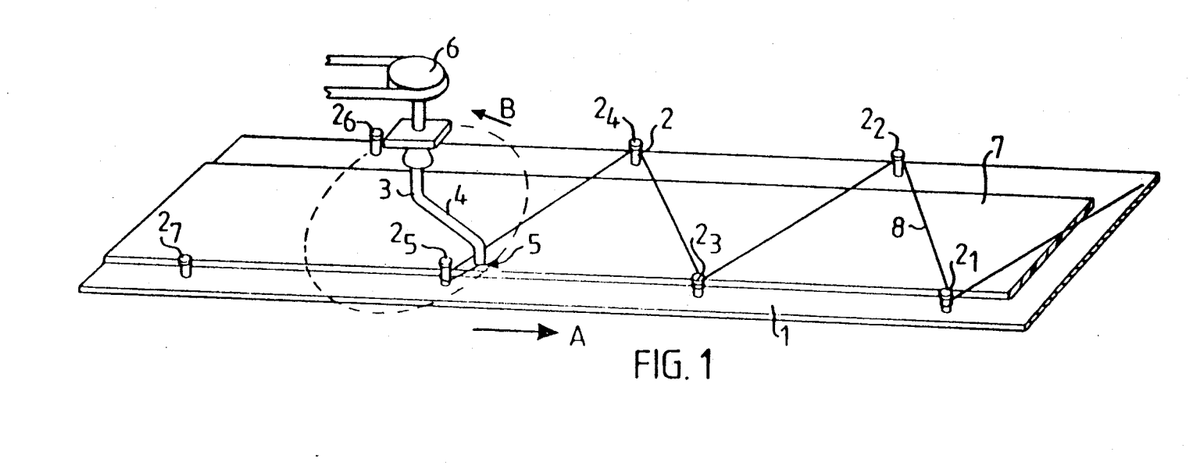
FIG. 1 is a schematic perspective view of a first embodiment of an inventive apparatus particularly suited for laying out elastic threads on a web of material.

FIG. 1 illustrates a conveyer path 1, which is driven in the arrowed direction A in some suitable manner, and which may comprise, for instance, a belt-driven endless path. Arranged in the close proximity of the two outer edges of the conveyer path are respective rows of thread dogging elements 2 in the form of pins, studs or like elements, the dogging elements 2 in one row being displaced in relation to the dogging elements in the opposite row, as seen in the direction of path movement. A rotatable thread outfeed device 3 is mounted on a frame, stand or like structure and is positioned such that its rotational axis will intersect the longitudinal symmetry line of the conveyer path. The thread outfeed device includes an outfeed tube 4 having an outlet 5 whose outlet orifice is located at a given distance above the upper surface of the conveyer path and radially outside the rotational axis of the thread outfeed device. The outfeed device is driven for rotation by means of an appropriate mechanism, such as a belt or sprocket wheel 6 and a transmission belt for instance.

The thread outfeed device 3 will also preferably be arranged to co-act with an ejector-type thread infeed device, the ejector effect generated by which is operative in blowing a free end of a thread in through the outfeed tube 4, and also with means for preventing slackening of the threads as they leave the outfeed device 3. When the thread outfeed device is intended for use with elastic threads, as in the case of the FIG. 1 embodiment, thread tension is preferably achieved with the aid of an unwinding reel or like device, which is driven such that the length of thread unwound from the reel per unit of time will be shorter than the length of thread fed out from the thread outlet. In the case of non-stretchable threads, the slack-preventing means may have the form of a simple friction brake. When laying out inelastic threads, it can also be appropriate to arrange a supplementary thread tensioning device downstream of the thread outlet, particularly in the case of those pattern formations in which not all of the closed loops formed are wound around dogging elements.

FIG. 1 also shows a material web 7 on which thread 8 exiting from the device 3 is intended to be affixed and which is advanced by means of the conveyer path 1.

The manner of operation of the inventive embodiment illustrated in FIG. 1 will now be described with reference to FIGS. 1 and 2

Figure 2:
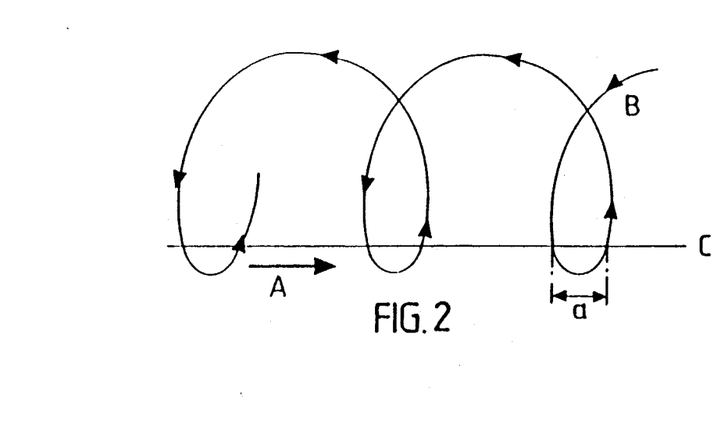
FIG. 2 illustrated the relative movement path of the thread outlet above the web.

FIG. 2 illustrates schematically a relative movement path taken by the thread outlet 5 over the conveyer path 1, when the thread outlet is rotated in the direction of the arrow B. The circular motion performed by the outlet is shown by a broken line in FIG. 1. Since during a first half of one revolution (in FIG. 1 the half revolution nearest the viewer) the outlet will have a movement component acting in the direction of conveyer path movement and during the second half of said revolution will have a movement component which is counter-directional to the linear movement of said path, movement of the conveyer path relative to the outlet will be greater per unit of time during that half revolution in which the outlet moves against the direction of path movement. The movement path described by the outlet will thus have the form of an extended flat spiral, above the conveyer path, as illustrated schematically in FIG. 2.

The V-shaped thread pattern shown in FIG. 1 is thus obtained by positioning the dogging elements 2 within the spiral-like movement path of the outlet, the dogging elements $2_1$, $2_3$, $2_5$, $2_7$ of FIG. 1 being placed in the closed loops formed in the spiral-like movement path of the thread outlet. Consequently, when the apparatus of FIG. 1 is operating, the thread 8 will be wound one turn around each of the dogging elements $2_1$, $2_3$, $2_5$ and $2_7$ on that side of the conveyer path on which the outlet has a movement component in the direction of movement of the conveyer path, and is laid around an outer peripheral part of the opposing dogging elements $2_2$, $2_4$ and $2_6$.

As beforementioned, the preferred thread outfeed device 3 is constructed so that the length of thread fed out with each revolution is shorter than the length corresponded by the sum of the distances between the dogging elements $2_1$, $2_2$ and $2_2$, $2_3$ respectively. As a result, the elastic thread 8 will be stretched as it is laid out, and will therefore always be brought into abutment with each dogging element that passes the outlet. This will ensure that the thread is unable to jump from a dogging element as a result of being subjected to the influence of external forces generated by vibration, shaking, air-draughts, etc.

It will also be understood that it is necessary for the outlet 5 to move more quickly than the conveyer path 1, in order that the outlet has time to pass a dogging element $2_1$, $2_3$, $2_5$ and $2_7$. Thus, if it is assumed that a point moves along the line C in FIG. 2, it will be seen to be necessary for the outlet to pass through that arcuate part of its movement path which lies beneath the line C in a faster time than the time taken for the conveyer path to move through the distance a, so that a point which is passed by the outlet on the upstream side will also be passed by the outlet on the downstream side, i.e. said point may not move at a speed which will enable said point to leave the movement path of the outlet.

Furthermore, the outlet 5 is located slightly above the plane of the conveyer path 1, such that the laid thread 8 will lie immediately above the web 7, but not in contact therewith, so as to enable any variations in thread outfeed speed, rotational speed, conveyer speed, and therewith variation in thread tension, to be equalized in the laid-out thread.

The thread laid in the V-shaped pattern shown in FIG. 1 is intended to be bonded or likewise affixed to the web 7. This can be effected readily, by pressing the thread against the web with the aid of a roller or like device arranged downstream of the apparatus shown in FIG. 1, and by adhesive bonding the thread to the web. The adhesive required herefor may be applied in conjunction with pressing the thread into contact with the web. It is preferred, however, to apply adhesive in a given pattern on the web 7, prior to passing the web to the conveyer path, at a location upstream of the apparatus shown in FIG. 1. Subsequent to bonding the threads to the web 7, the threads are clipped from those sections of the conveyer path which protrude beyond the web.

Figure 3:
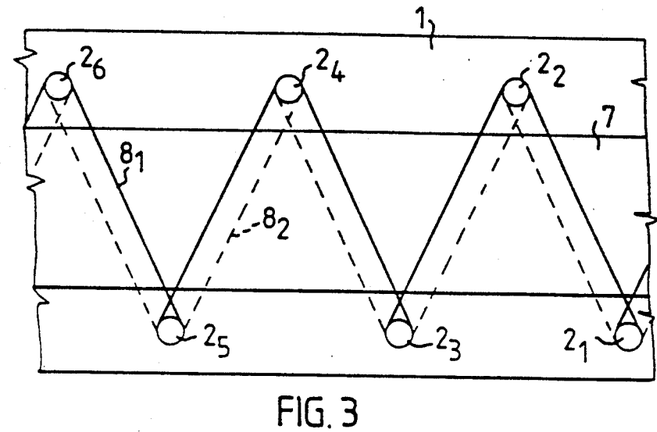
FIG. 3 is a schematic illustration of a thread pattern in which threads are laid with the aid of two thread outfeed devices which rotate in mutually opposite directions and which form part of the apparatus illustrated in FIG. 1.

FIG. 3 illustrates the pattern obtained when a second or further thread outfeed device is mounted in the travel direction, on one side of the first mentioned thread outfeed device 3 illustrated in FIG. 1, this second thread outfeed device being arranged to rotate in a direction opposite to the first device. The thread $8_1$ laid out by the first device 3 is shown in a full line, whereas the thread $8_2$ laid out by the second device 3 is shown in a broken line. Because the second thread outfeed device 3 rotates in a direction opposite to the arrow B, the thread $8_2$ will be wound around the dogging elements $2_2$, $2_4$ and $2_6$ instead of around the dogging elements $2_1$, $2_3$ and $2_5$, the thread $8_1$ exiting from the first thread outfeed device being wound around these latter dogging elements in the manner aforedescribed. Thus, as will be seen from FIG. 3, the threads $8_1$ and $8_2$ extend parallel with one another within the region of the web 7. Consequently, a V-shaped double elastic can be produced very readily with the aid of the inventive apparatus.

Figure 4A:
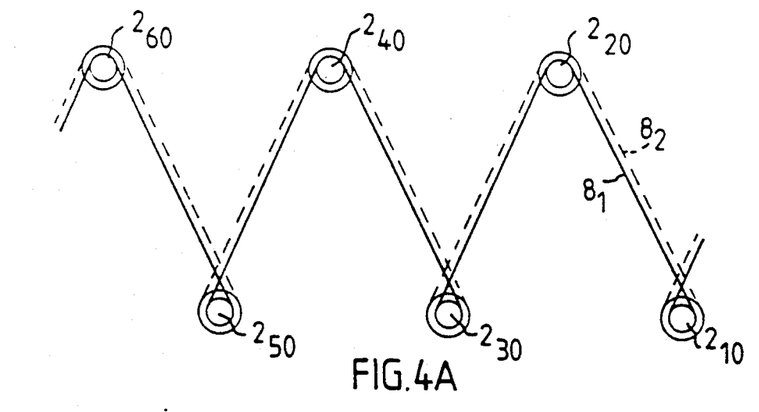
FIGS. 4A and 4B illustrate the thread pattern obtained when using two thread outfeed devices which rotate in mutually the same direction and which form part of the apparatus illustrated in FIG. 1, said apparatus also including thread dogging elements of particular configuration, the profiled section of which dogging elements is shown in FIG. 4B.
Figure 4B:
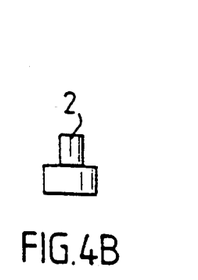

Double elastic can also be produced with the aid of two thread outfeed devices which rotate in mutually the same direction, when the dogging elements used have varying height dimensions and when the two threads are caused to exit from respective devices at mutually different heights, i.e. respective thread outlets are positioned at different heights above the conveyer path. FIG. 4A illustrates one such thread pattern, and FIG. 4B illustrates in side view a dogging element of which the upper part has smaller dimensions than the lower part thereof.

Figure 5:
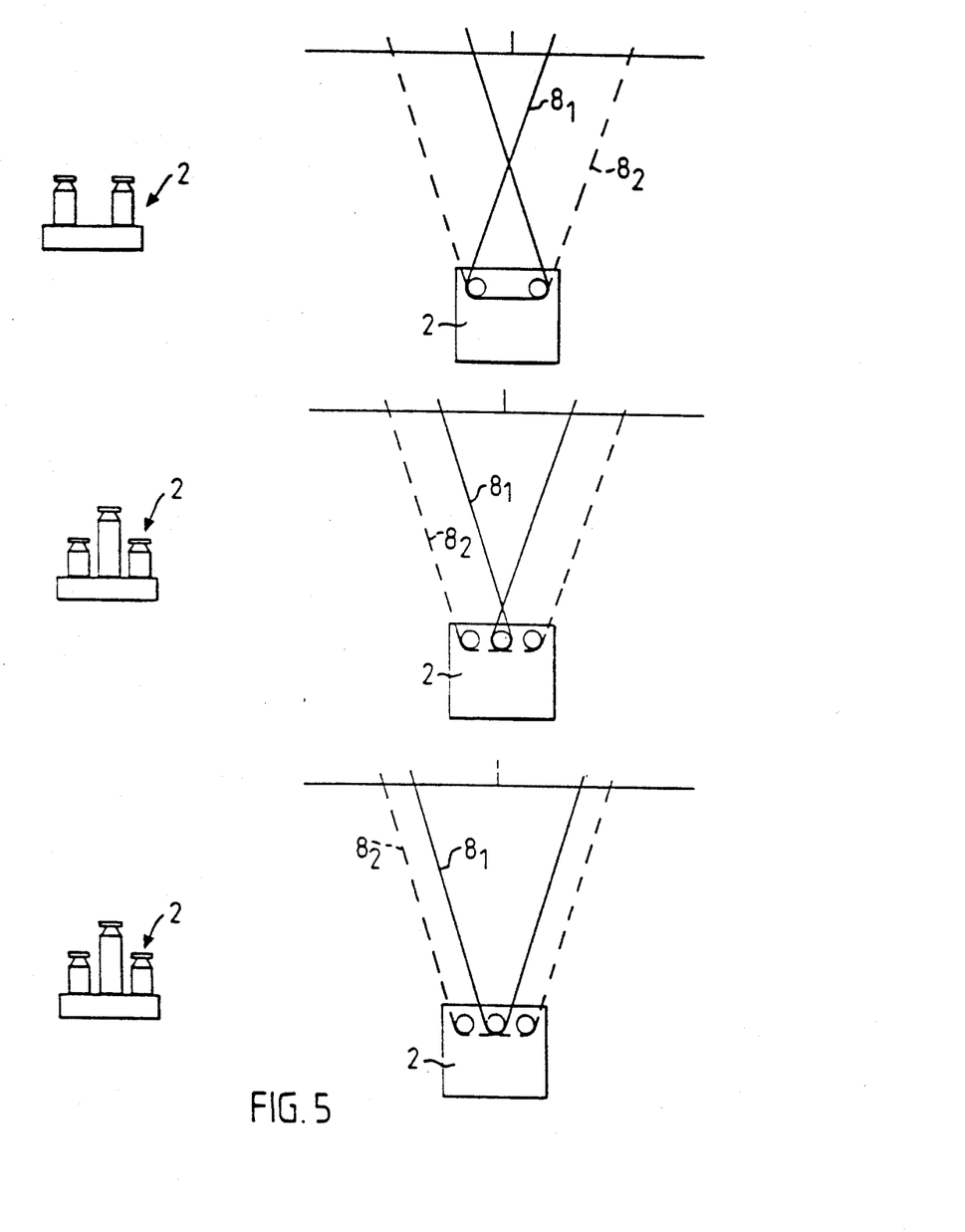
FIG. 5 illustrates the configurations of various dogging elements, to the left of the Figure, and a thread pattern obtained when using said elements, to the right of the Figure.

The left-hand side of FIG. 5 illustrates in side view other dogging element configurations, while shown to the right in FIG. 5, from above, are thread patterns $8_1$, $8_2$ obtained with the aid of such elements. The dogging element shown at the top of the figure can replace the type of dogging element illustrated in FIG. 3, whereas the dogging element shown to the bottom of the Figure can replace the type of dogging element illustrated in FIGS. 4A and 4B. When comparing the centre and bottom views shown in FIG. 5, these views being taken from above and illustrating part-patterns produced by thread outfeed devices which rotate in mutually different directions and mutually the same directions respectively, that it is possible with such dogging elements to lay the threads at different distances between mutually parallel threads, in dependence on the directions in which the thread outfeed devices rotate.

A study of FIG. 5 will also show that the threads can be laid in a trapezoidal configuration, by exchanging the dogging elements $2_2$, $2_4$, $2_6$ of the FIG. 1 embodiment with two mutually adjacent and mutually spaced dogging elements in the movement direction of the conveyer path, provided that these dogging elements are positioned within the movement path of the outlet.

Of course, it is also possible to produce regular patterns, the recurring parts of which are formed during more than one revolution of the outlet. Thus, if the dogging element $2_3$ is removed from the FIG. 1 apparatus, the thread 8 will move parallel with the direction of conveyer path movement, between the dogging elements $2_2$ and $2_4$ when the outlet 5 has reached the position illustrated in FIG. 1, and the thread will thus be laid in a U-shape between the dogging elements $2_1$, $2_2$, $2_4$ and $2_5$. If the dogging element $2_4$ is removed instead of the dogging element $2_3$, the thread 8 will run parallel with the direction of conveyer path movement, between the dogging elements $2_3$ and $2_5$, in a manner analogous with the former case.

Figure 6:
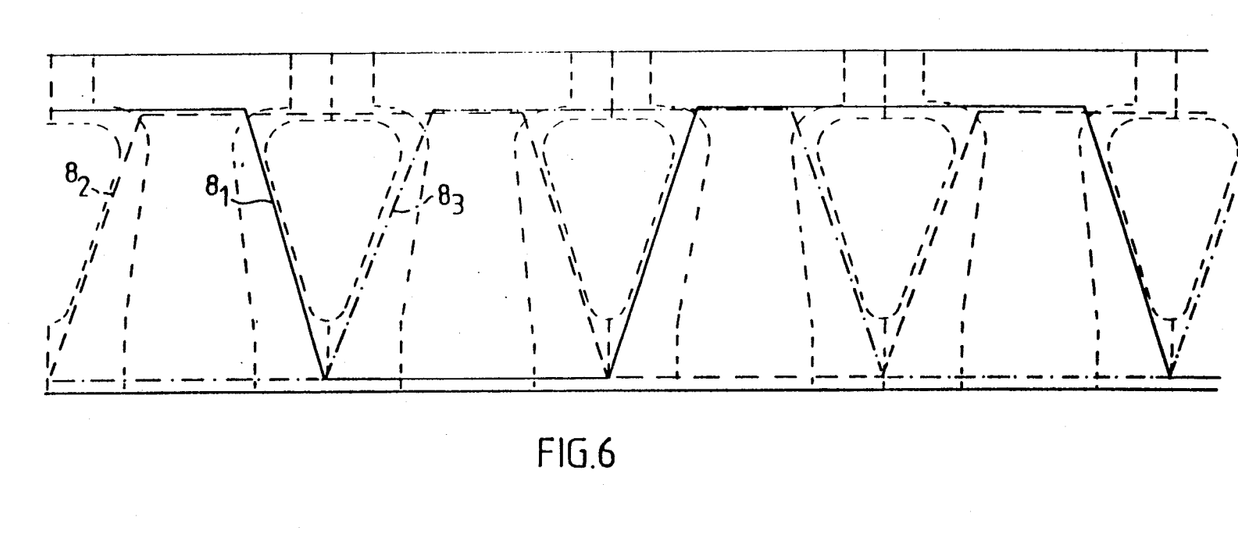
FIG. 6 illustrates a three-thread pattern which can be employed very advantageously for the purpose of laying out diaper leg and waist elastic.

FIG. 6 illustrates a pattern which is formed by three different threads $8_1$, $8_2$, $8_3$, which have a square-wave-like configuration and which are displaced in phase relative to one another, these threads being shown as a full line thread $8_1$, a broken line thread $8_2$ and a dotted line thread $8_3$. Also shown in dotted, fainter lines in the Figure, is the configuration of the diapers on which the three threads are intended to form leg and waist elastics. The three threads are fed-out at mutually different heights above the web, so that a dogging element or like thread guide which co-acts with solely one of the threads is unable to disturb the laying out of the other threads. Thus, the inventive apparatus enables longitudinal and transverse elastic to be laid out simultaneously, which considerably increases the production rate in comparison with those cases when the longitudinal and transverse elastics must be laid out in separate steps. Furthermore, it is possible, of course, to form patterns from more than three threads, and two conveyer paths can be used when laying out the threads, these paths being later brought together.

Figure 7:
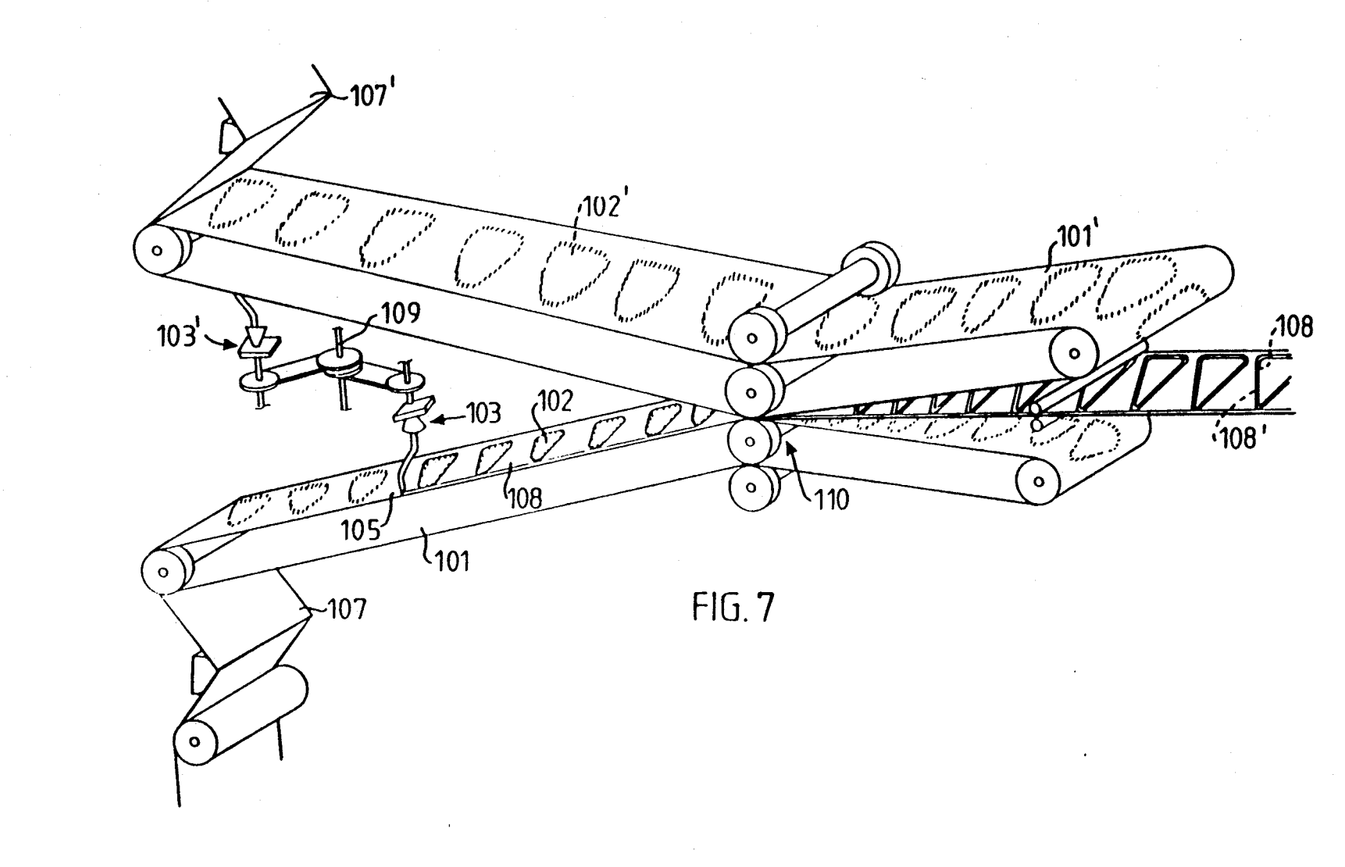
FIG. 7 illustrates a second embodiment of inventive apparatus by means of which threads are laid out in a curved pattern.

FIG. 7 illustrates another embodiment of inventive apparatus in which two conveyer paths are used and which differs from the apparatus illustrated in FIG. 1 by virtue of the fact that the dogging elements are arranged close together in mutually sequential groups 102, 102', so that the threads will form curved patterns.

In other respects, the threads are laid out in a manner analogous with that described with reference to FIGS. 1 and 2, with the principle difference that more than one dogging element is positioned within the closed loops of the outlet movement path, which means that the length and breadth extension of the dogging element groups must be taken into account when deciding the relationship between the speed of movement of the conveyer path 101 and the rotational speed of the thread outfeed device 103.

In order to ensure that the outlet 105 is able to pass on both sides of the dogging element group 102 during rotational movement of the outlet, it is necessary for the outlet of the FIG. 7 embodiment to rotate more quickly in relation to the moving conveyer path than the outlet 5 of the FIG. 1 embodiment.

Figure 8:
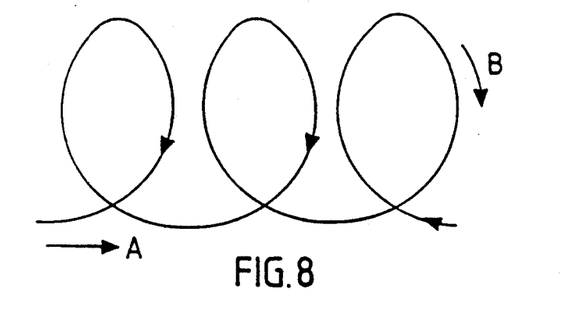
FIG. 8 illustrates the relative movement path of a thread outlet located above the material web and included in the apparatus shown in FIG. 7.

FIG. 8 illustrates schematically the relative movement path of the outlet 105 on the conveyer path 101. As a comparison with FIG. 2 will show, the illustrated movement paths of the outlets 5 and 105 have principly the same spiral-like configuration, although the spiral shape described by the outlet 5 is more extended than the spiral-shaped movement path of the outlet 105, due to the differences in rotational speed relative to the speed of conveyer path movement.

The dogging element groups 102 have a droplet configuration, with a wider and a narrower part relative to a line which extends parallel with the direction of conveyer movement and which is intersected by the rotational axis of the thread outfeed device 103. The rotational direction of the outlet is preferably chosen so that that part of its revolutionary movement in which the outlet has a movement component in the direction of conveyer movement is located on the same side of the aforesaid line as the broader part of the droplet configuration formed by the dogging element group 102.

The apparatus illustrated in FIG. 7 is constructed to lay a pattern of two mutually parallel threads and to apply these threads between two material webs 107 and 107', which are moved past two glue nozzles respectively, prior to being brought together and placed on two conveyer paths in the form of belt or chain driven endless belts 101 and 101'. The dogging element groups 102 and 102', rigidly mounted on the endless belts, pass through the webs such as to project above the webs to a height which will prevent the laid-out threads from coming into contact with the adhesive earlier applied to the web surfaces. The dogging element groups 102 and 102' will pass successively beneath associated, rotating thread outfeed devices 103 and 103', which are driven synchronously by a common drive shaft 109. The material webs 102 and 102' and the overlying threads 108 and 108' then pass through a press section 110, in which the material webs and the intermediate threads are pressed together and exit from the press section in the form of a double-layer material structure with intermediate double elastic. It is mentioned that the term "overlying" used in conjunction with the outfeed of threads is related to the side of an endless belt on which the threads are laid, this side constituting in this text the upper side, irrespective of whether said side is in reality the upper or the lower side of the belt.

As will be seen from FIG. 7, the conveyer belts 101 and 101' move in a divergent path subsequent to exiting from the press section, such as to withdraw the dogging elements successively from piercing engagement with the material webs 107 and 107'. The rollers mounted in the press section 110 are recessed in the vicinity of the dogging elements, so as not to damage said elements.

In those instances when compression of the parts of the webs lying laterally outside the dogging elements does not induce sufficient compression of intermediate parts such as to achieve positive adhesion of the threads, the rollers may be provided with grooves opposite each pair of dogging elements in the groups 102 and 102' coinciding in the longitudinal direction of the conveyer path. One conceivable variant is to provide a dogging element construction in which the dogging elements can be withdrawn down into the confines of the conveyer path and biassed towards their working position by means of a spring.

It should be mentioned that the aforementioned configuration of press rollers or dogging elements can be applied with all pattern configurations in which dogging elements pierce through the applied material layers, such as in the case of the pattern illustrated in FIG. 6 for instance.

It should also be mentioned in this respect that the amplitude of the relative movement path of the outlet on the conveyer path can, of course, be varied by changing the radial length of the outfeed tube and by placing the rotational centre of the thread outfeed device to one side of the longitudinal symmetry line of the conveyer path.

In the case of the embodiments described hitherto, the thread outlet performs a simple rotating movement. However, those variations in the outlet movement path afforded by varying the relationship between the speed at which the outlet rotates and the speed at which the conveyer path moves, or by changing the radial length of the outfeed tube, will not always suffice in achieving the desired thread lay-out pattern. The possibilities of varying the thread lay-out pattern can be improved, by configuring the thread outfeed device in accordance with the device illustrated schematically from above in FIG. 9. In the case of this embodiment, the rotation axle of the outfeed tube 204 is firmly connected to a gear or toothed wheel 209 and axially rigid but rotatably connected to the free end of a rotatable arm 210. The teeth of the toothed wheel 209 co-act with the radially inner teeth of a gear-ring or toothed ring 211, which in the case of the preferred embodiment is stationary. Thus, rotation of the arm 210 in the direction indicated by the arrow D will cause the toothed wheel to rotate about its own axis, by virtue of co-action with the toothed ring, which means, in turn, that the thread outlet will rotate in the direction of the arrow E. When the transmission ratio between toothed ring and toothed wheel is 1:3, the outlet will rotate three times about its own rotational axis for each revolution of the arm 210.

Figure 9:
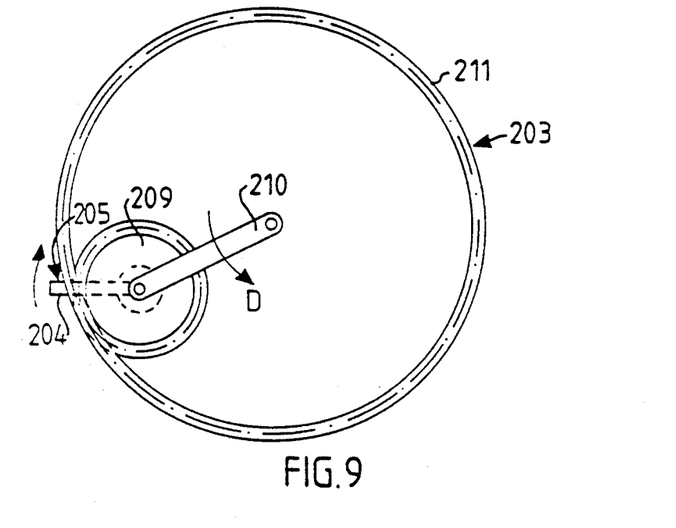
FIG. 9 illustrates a second embodiment of an inventive thread outfeed device.
Figure 10:
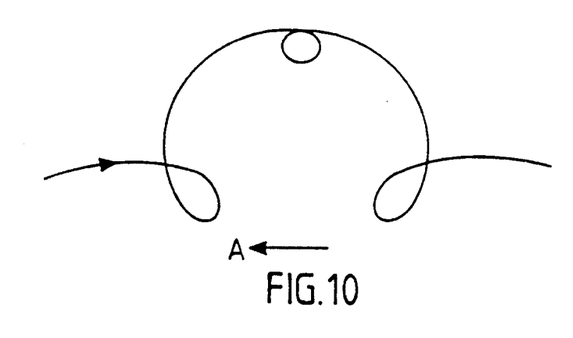
FIG. 10 illustrates the relative movement path of the thread outlet of FIG. 9 above a continuous web.

FIG. 10 illustrates schematically the relative movement path of the thread outlet on a conveyer path moving in the direction of the arrow A. This movement path enables the number of possible pattern configurations to be increased considerably. For example, a thread outfeed device according to FIG. 9 can be used with great advantage to form square-wave patterns, such patterns being difficult to achieve with thread outlets which are solely capable of performing simple rotational movements.

By varying the transmission ratio between the toothed ring and the toothed wheel and the length of the outfeed tube of the thread outfeed device, the thread outfeed device illustrated in FIG. 9 can be used to produce a large number of different thread lay-out patterns.

Furthermore, it is also possible in this respect to change the transmission ratio, by rotating the toothed wheel at the same time as the arm 210.

As will be understood, the threads laid out by means of the aforedescribed embodiments of the inventive apparatus are not restricted in use to the leg and waist elastic of diapers, and neither need they necessarily be bonded to a flat material layer.

Accordingly, an application of the inventive concept in which a thread laid out in a square wave pattern is wound one revolution around a cylindrical object will now be described with reference to FIG. 11.

Figure 11:
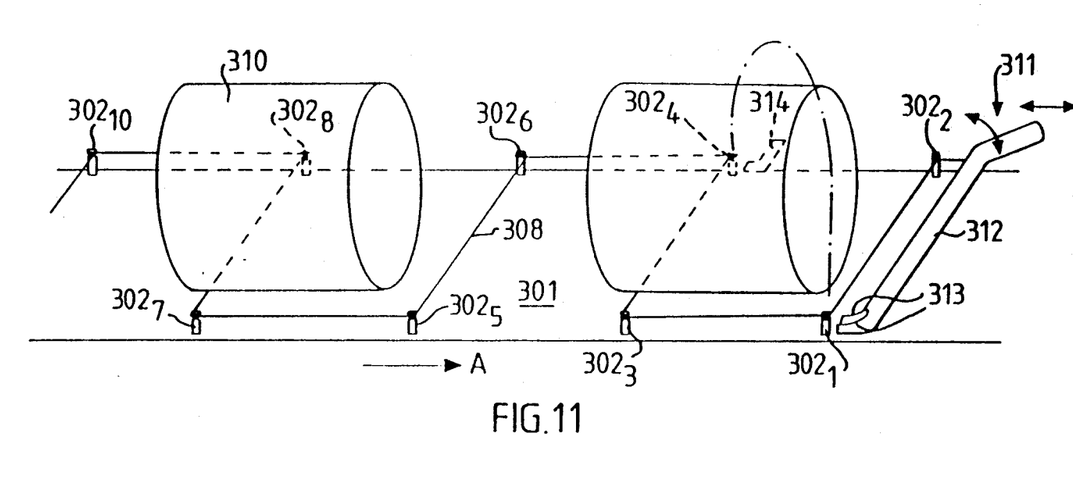
FIG. 11 illustrates an application in which a laid-out thread pattern is utilized to wind a thread around a cylindrical object.

In FIG. 11 there is shown a conveyer path 301 on which a thread 308 is laid out in a square wave pattern with the aid of a thread outfeed device (not shown) of the kind illustrated in FIG. 9. Positioned on the conveyer path above the thread pattern are cylindrical bodies 310, as shown in FIG. 11. It will be understood that the cylindrical bodies are illustrated by way of example and that said bodies may have any cross-sectional shape whatsoever. The apparatus illustrated in FIG. 1 also includes a gripping device 311 which is intended to co-act with each alternate dogging element $302_1$, $302_5$ etc nearest the viewer of FIG. 11, in a manner described in more detail hereinafter.

The gripping device 311 can be swung through 180°, between a first and a second terminal position, about an axis which lies in the extension of an imaginary line passing through the dogging elements $302_3$ and $302_2$, and thus has an angle of 45° to the direction of conveyer path movement. The gripping device comprises an arm 312 which in the terminal position shown in FIG. 11 extends transversely across the conveyer path and includes two gripping fingers 313, which in the illustrated position lie opposite the dogging element $302_1$. In the other terminal position of the gripping device, the arm 312 extends parallel with the direction of conveyer path movement.

The conveyer path moves in the direction of the arrow A and the dogging element $302_1$ will thus be moved in between the fingers 313. This will cause the arm 312 to be rotated through 180°, from the terminal position shown in FIG. 11 to the other terminal position, and the dogging element $302_1$, which is constructed so as to be liftable from the conveyor path, will accompany movement of the arm. The dogging element $302_1$ will therefore be moved around a semicircular path, as indicated in chain lines in FIG. 11, to the position occupied by the dogging element $302_4$ in the Figure. At the same time, the dogging element $302_4$ is moved together with the conveyer path, and the dogging element $302_1$ will thus be located immediately behind the dogging element $302_4$ when the arm 312 has reached its other terminal position. The arm 312 is then rotated back to its first terminal position, wherewith the thread 308 can be withdrawn from the dogging element $302_1$, by virtue of the fact that at this time point the thread is located beneath the short leg of an L-shaped thread stripper 314. During reverse pivotal movement of the arm 312, the gripping device 311 is moved forwards, parallel with the conveyer path, so that the dogging element $302_1$ can be moved back to the same location on the conveyer path. Subsequent hereto, the gripping device is again moved forwards, so that the gripping fingers leave the dogging element $302_1$ and the arm 312 is then again rotated to its second terminal position and moved backwards, through the same distance as it was earlier moved forwards. When the whole of the cylinder body has passed the axle connection of the gripping device 311, the arm 312 is again rotated to the position shown in FIG. 11, so as to be able to co-act with the dogging element 302₅. When the aforedescribed operation is completed, the thread 308 will thus have been wound through one turn around the cylinder 310.

Figures 12, 13:
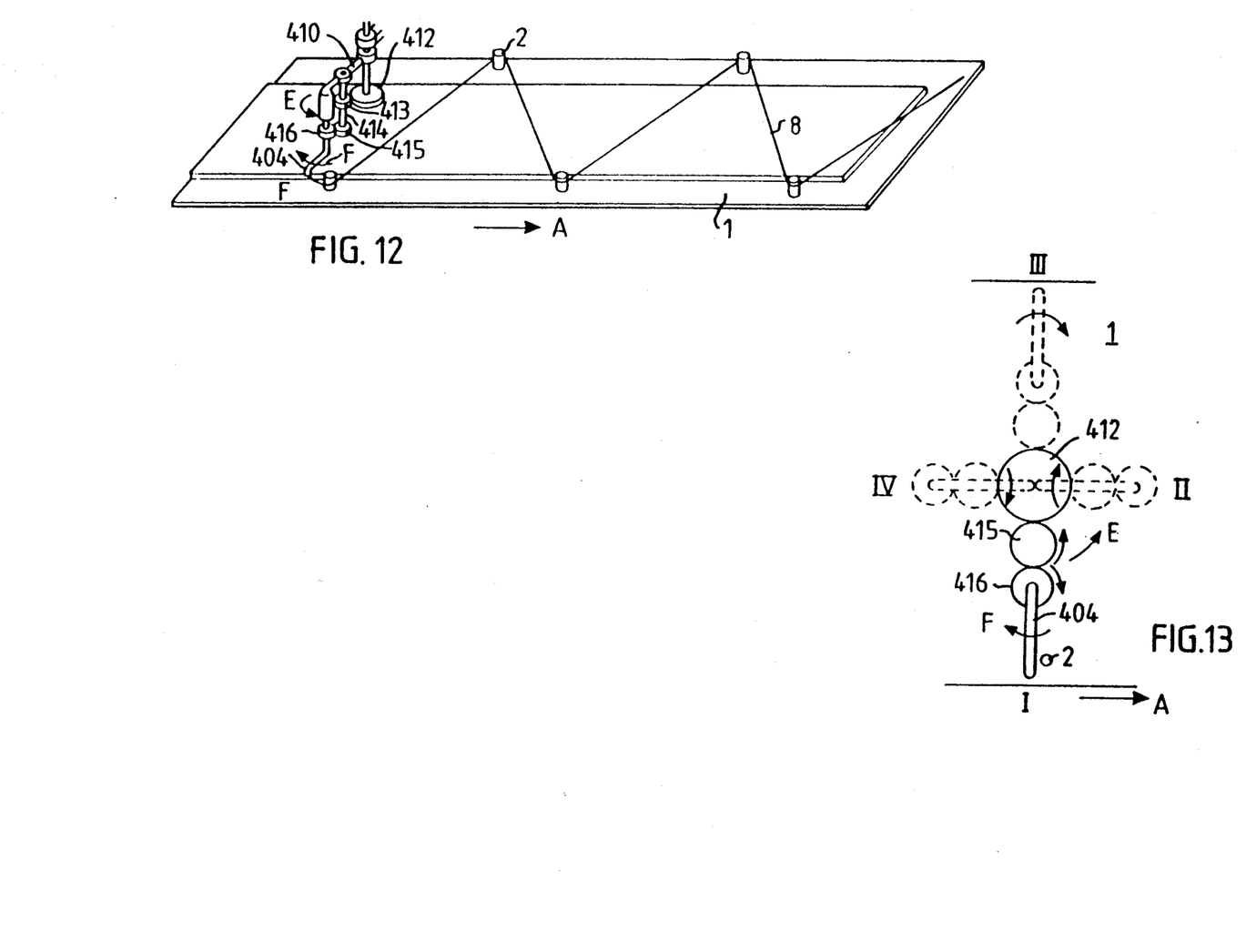
FIGS. 12 and 13 illustrates a third embodiment of an inventive thread outfeed device.

FIGS. 12 and 13 illustrate schematically an embodiment of a thread outfeed device which is particularly suitable for laying out threads in triangular patterns.

In the case of this embodiment, an outfeed tube 404 is carried for rotation by a carrier 410 which can be rotated about a shaft 411 in some suitable manner, for instance by means of a belt transmission. A toothed wheel 412 is rigidly connected to the shaft 411 and engages a toothed wheel 413 which is rigidly connected to a further shaft 414, which in turn is carried for rotation by the carrier arm 410. Mounted on the lower end of the shaft 414 is a toothed wheel 415 which, similar to the toothed wheel 413, is rigidly connected to the shaft 414. This toothed wheel 415 is in engagement with a toothed wheel 416, which is rigidly connected to the outfeed tube 404, such as to rotate said tube relative to the carrier arm 410.

The composite movement of the outfeed tube 404 resulting from rotation of the carrier arm 410 in the direction of the arrow E will now be explained with reference to FIG. 13, in which the toothed wheels 412, 415 and 416 have been symbolized with circles for the sake of simplicity.

FIG. 13 shows the outfeed tube 404 and the toothed wheels 412, 415 and 416 in four mutually different, equally spaced positions I–IV during a revolution of the carrier arm 410. The position I is shown in full lines and corresponds to the position of the outfeed tube 404 shown in FIG. 12. Rotation of the carrier arm 410 in the direction E will cause the toothed wheel 413 to be rotated by the fixed toothed wheel 412 in an anti-clockwise direction in FIGS. 12 and 13, which in turn means that the toothed wheel 415 will also rotate anti-clockwise and therewith cause the toothed wheel 416 and the outfeed tube 404 to rotate clockwise. The gear transmission is therewith so constructed that when the carrier arm 410 is rotated through one quarter of a revolution and has reached the position II in FIG. 13, the toothed wheel 416 will also have rotated through one quarter turn. As will best be seen from FIG. 13, the outfeed tube 404 has a length such that in the position II the end of the tube will exactly reach the centre of the toothed wheel 412.

Subsequent to a further quarter turn of the carrier arm 410, and therewith also of the toothed wheel 416, the outfeed tube is again perpendicular to the longitudinal axis of the path 1 and the end of the tube will extend slightly beyond the movement path of the dogging elements 2. In position III, the outfeed tube, similar to the position II, extends parallel with the longitudinal direction of the web 1.

Because of the configuration of the thread outfeed device, the end of the outfeed tube 404 will move in a rectilinear, reciprocating movement path transversely across the conveyer path 1. As will be seen from FIG. 12, when laying out threads with the aid of such a device, the thread 8 will not be crossed at any of the dogging elements, as distinct from the case when using the aforedescribed thread outfeed devices, see FIG. 1 and FIG. 11. The obtainment of uniform thread tension is facilitated by this device.

Thus, the invention provides apparatus which enable threads to be laid out at high speeds without the need of complicated thread guides, while still enabling various thread patterns to be readily achieved. Although the method and apparatus according to the invention are primarily intended for laying out threads intended for use as leg and waist elastic in diapers, it will be understood that the invention is not restricted to such use. The invention shall therefore only be limited by the disclosures made in the following claims.

We claim:

1. A method of positioning at least one filament in a predetermined pattern over a wide web of sheet material carried on a conveyor comprising the steps of:
   rotating a first filament outlet of a filament outfeed device in a plane which is substantially parallel to said conveyor, wherein said first filament outlet is tubular;
   said rotation of said first filament outlet including simultaneous rotation of said first filament outlet about both a first and a second rotational axis wherein the first rotational axis and the second rotation axis are parallel to each other and transverse to said plane and the first filament tubular outlet rotates about the first rotational axis while the second rotational axis rotates about the first rotational axis;
   outfeeding said filament through said first filament outlet; and
   linearly moving said conveyor relative to said first and second rotational axes such that said filament is wrapped around dogging elements on said conveyor to position said filament on said web in said predetermined pattern.

2. A method as claimed in claim 1 wherein said filament is selected from the group consisting of elastic thread and elastic band.

3. A method as claimed in claim 1 further comprising the step of maintaining the filament in a tensioned state as said filament is being wrapped around said dogging elements.

4. A method as claimed in claim 1 further comprising the step of rotating a second filament outlet of a filament outfeed device in a direction opposite to a direction of rotation of said first filament outlet such that said predetermined pattern includes double parallel filaments, said second filament outlet being positioned downstream from said first filament outlet.

5. A method as claimed in claim 1 wherein said predetermined pattern is a square-wave pattern.

6. A method as claimed in claim 5 further comprising the step of rotating at least a second and a third filament outlet such that said predetermined pattern is a multiple square-wave pattern having a sequence of pattern segments comprising a trapezoid and a triangle over said web.

7. A method as claimed in claim 6 wherein the dimensions of said pattern segments are chosen to have a size suitable for a leg and waist elastic of a diaper.

8. A method as claimed in claim 6 wherein each of said filaments is laid out in a different plane over said web.

9. A method of positioning at least two filaments in a predetermined pattern between two webs, each web carried on a different conveyor, said conveyors positioned to converge and then diverge along a direction of movement of said conveyors, said method comprising the steps of:

rotating two filament outlets, one filament outlet being positioned in a plane of rotation over one conveyor, the other filament outlet being positioned in a plane of rotation over the other conveyor, each plane of rotation being substantially parallel to a portion of its corresponding conveyor;

outfeeding a filament through each of said two filament outlets;

linearly moving both of the conveyors relative to said two filament outlets such that the filament from the one filament outlet wraps around dogging elements disposed on the one conveyor and is positioned in a predetermined pattern on the one conveyor and such that the filament from the other filament outlet wraps around dogging elements on the other conveyor and is positioned in a predetermined pattern on the other conveyor; and pressing said two webs together at an apex region of said two conveyors, said filaments being positioned between the two webs.

10. A method as claimed in claim 9 wherein said filaments are selected from the group consisting of elastic threads or bands.

11. A method as claimed in claim 9 further comprising the step of bonding said webs together.

12. A method as claimed in claim 11 wherein said bonding step is performed with glue.

13. An apparatus for positioning a filament in a predetermined pattern over a web carried on a conveyor comprising:

dogging elements disposed on said conveyor and movable with said web, and first means for wrapping the filament around the dogging elements to provide said predetermined pattern over said web, said wrapping means including means for simultaneously rotating at least one filament outlet about a first and second rotational axis in a plane substantially parallel to said conveyor wherein said at least one filament outlet is tubular and the first rotational axis and the second rotational axis are parallel to each other and transverse to said plane, said means for simultaneously rotating including means for rotating the at least one tubular filament outlet about the second rotational axis while the second rotational axis rotates about the first rotational axis.

14. An apparatus as claimed in claim 13 further comprising means for maintaining tension in said filament when said filament is wrapped around said dogging elements.

15. An apparatus as claimed in claim 13 further comprising second means for wrapping a second filament around said dogging elements over said web, said second means for wrapping a second filament being disposed downstream from said first means for wrapping a filament, said second means for wrapping including means for synchronously driving said second means for wrapping in a different rotational direction from said first means for wrapping.

16. An apparatus as claimed in claim 13 wherein said first means for wrapping the filament includes:

a carrier arm, rotatable in a first direction, said at least one filament outlet being disposed on said carrier arm; and means for rotating said filament outlet in a second direction which is opposite to said first direction of said carrier arm.

17. An apparatus as claimed in claim 13 wherein said dogging elements are arranged in a row along each outer edge of the conveyor with a space between each dogging element.

18. An apparatus as claimed in claim 13 wherein said means for simultaneously rotating said filament outlet about two rotational axes includes:

a rotatable arm having a free end and a rotatably fixed end;

a stationary toothed ring having teeth on its inside circumference;

a rotatable toothed wheel having teeth which engage the teeth on the toothed ring, said toothed wheel being rotatably attached at its center on one side to the free end of the rotatable arm and fixedly connected at its center on the other side to said at least one filament outlet.

19. An apparatus for positioning at least two filaments in a predetermined pattern between two webs comprising:

a first conveyor for carrying a first web;

a second conveyor for carrying a second web;

said first and second conveyors positioned to converge toward each other upstream of an apex region, said first and second conveyors positioned to diverge from each other downstream of said apex region;

a plurality of dogging elements disposed on each conveyor and movable with said web;

first means for wrapping at least one filament around dogging elements of said first conveyor such that said predetermined pattern is formed over said first conveyor, said first wrapping means including a filament outlet;

second means for wrapping at least one filament around dogging elements of said second conveyor such that said predetermined pattern is formed over said second conveyor; and means for pressing the webs together near said apex region, said filaments being positioned between said webs.

20. An apparatus as claimed in claim 19 further comprising means for bonding said webs together.

21. An apparatus as claimed in claim 19 wherein said predetermined pattern is a multiple square-wave pattern which includes a sequence of pattern segments comprising a trapezoid and a triangle.

22. An apparatus as claimed in claim 19 wherein at least one of said dogging elements has a cross-sectional dimension which varies along an axis of said at least one dogging element.

23. An apparatus as claimed in claim 22 wherein said dogging elements comprise superposed cylindrical parts having different diameters.

24. An apparatus as claimed in claim 22 wherein said at least one dogging element comprises a filament receiving grove provided peripherally thereon.

25. An apparatus as claimed in claim 19 wherein at least one of said dogging elements comprises two cylindrical parts arranged side by side.

26. An apparatus as claimed in claim 25 wherein said at least one of said dogging elements comprises a third cylindrical part, arranged between said two cylindrical parts, which extends above said two cylindrical parts.

27. An apparatus as claimed in claim 13 wherein at least one of said dogging elements has a cross-sectional dimension which varies along an axis of said at least one dogging element.

28. An apparatus as claimed in claim 27 wherein said at least one dogging element comprises superposed cylindrical parts having different diameters.

29. An apparatus as claimed in claim 27 wherein said at least one dogging element comprises a filament receiving grove provided peripherally thereon.

30. An apparatus as claimed in claim 13 wherein at least one of said dogging elements comprises two cylindrical parts arranged side by side.

31. An apparatus as claimed in claim 30 wherein said at least one of said dogging elements comprises a third cylindrical part, arranged between said two cylindrical parts, which extends above said two cylindrical parts.

* * * * *